(12) United States Patent
Sullivan et al.

(10) Patent No.: US 7,789,826 B2
(45) Date of Patent: Sep. 7, 2010

(54) MANUALLY CONTROLLED ENDOSCOPE

(75) Inventors: Roy Sullivan, Millville, MA (US); Eric Litscher, Hopkinton, MA (US); Vincent Turturro, Marlboro, MA (US); Matt Whitney, Upton, MA (US)

(73) Assignee: Boston Scientific Scimed, Inc., Natick, MA (US)

(*) Notice: Subject to any disclaimer, the term of this patent is extended or adjusted under 35 U.S.C. 154(b) by 762 days.

(21) Appl. No.: 10/955,910

(22) Filed: Sep. 30, 2004

(65) Prior Publication Data

US 2006/0069311 A1    Mar. 30, 2006

(51) Int. Cl.
*A61B 1/00* (2006.01)

(52) U.S. Cl. ............... 600/149; 600/139; 600/146; 600/147; 600/150; 600/152

(58) Field of Classification Search ......... 600/146–147, 600/149–150, 152
See application file for complete search history.

(56) References Cited

U.S. PATENT DOCUMENTS

| | | | |
|---|---|---|---|
| 3,557,780 A | 1/1971 | Sato | |
| 4,111,190 A * | 9/1978 | Plumridge | 600/435 |
| 4,207,873 A | 6/1980 | Kruy | |
| 4,294,233 A | 10/1981 | Takahashi | |
| 4,461,282 A | 7/1984 | Ouchi et al. | |
| 4,483,326 A | 11/1984 | Yamaka et al. | |
| 4,557,254 A * | 12/1985 | Yamaguchi | 600/149 |
| 4,714,075 A | 12/1987 | Krauter et al. | |
| 5,007,406 A | 4/1991 | Takahashi et al. | |
| 5,299,559 A * | 4/1994 | Bruce et al. | 600/141 |
| 5,373,317 A | 12/1994 | Salvati et al. | |
| 5,496,260 A | 3/1996 | Krauter et al. | |
| 5,931,833 A | 8/1999 | Silverstein | |
| 6,709,667 B1 * | 3/2004 | Lowe et al. | 424/422 |
| 2004/0073083 A1 | 4/2004 | Ikeda et al. | |

* cited by examiner

*Primary Examiner*—Matthew J Kasztejna
(74) *Attorney, Agent, or Firm*—Finnegan, Henderson, Farabow, Garrett & Dunner, LLP

(57) ABSTRACT

A control handle for use with a steerable endoscopic device. The endoscopic device having a pair of control wires to effect steering. The control handle includes a steering mechanism that includes an actuator, such as a control knob, drivingly connected to a drive member, such as a sprocket or drive gear. To transmit force from the drive member to the control wires, a length of transmission structure, such as bead chain, is connected to the proximal ends of the control wires and is engaged with the drive member. In one embodiment, a single-use endoscope may be provided, which includes a control handle, a steerable endoscopic device, and a umbilical cord or communications conduit for functionally connecting the control handle to a control cabinet of an endoscopic imaging system.

15 Claims, 6 Drawing Sheets

MANUALLY CONTROLLED ENDOSCOPE

FIELD OF THE INVENTION

In general, the present invention is directed to devices suitable for use in medical procedures, and in particular, control units, such as control handles, for manually deflecting the distal end of an associated steerable medical device.

BACKGROUND OF THE INVENTION

It has become well established that there are major public health benefits from regular endoscopic examinations as an aid to the early detection of disease of internal structures such as the alimentary and excretory canals and airways, e.g., the colon, esophagus, lungs, uterus, bladder, bronchi, and other organ systems. A conventional imaging endoscope used for such procedures comprises a flexible tube with a fiber optic light guide that directs illuminating light from an external light source to the distal tip where it illuminates the region (i.e. tissue, occlusion object) to be examined. Frequently, additional optical components are incorporated to adjust the spread of the light exiting the fiber bundle and the distal tip. An objective lens and fiber optic imaging light guide communicating with a camera at the proximal end of the scope, or an imaging camera chip at the distal tip, produce an image that is displayed to the operator. In addition, most endoscopes include one or more working channels through which medical devices such as biopsy forceps, snares, fulguration probes, and other tools may be passed.

Navigation of the endoscope through complex and tortuous paths is critical to success of the examination with minimum pain, side effects, risk, or sedation to the patient. To this end, modern endoscopes include means for deflecting the distal tip of the scope to follow the pathway of the structure under examination, with minimum deflection or friction force upon the surrounding tissue, and to survey targeted examination sites. Control cables similar to bicycle brake cables are carried within the endoscope body in order to connect a flexible portion of the distal end to a set of control knobs at the proximal endoscope handle. By manipulating the control knobs, the operator is usually able to steer the endoscope during insertion and direct it to a region of interest.

SUMMARY OF THE INVENTION

In accordance with aspects of the present invention, a control device is provided. The control device includes at least one pair of control wires for deflecting the distal end of an associated device, such as a medical device. The control device also includes a housing configured for receiving the pair of control wires, transmission structure having first and second ends coupled to the ends of the pair of control wires, and a drive member carried by the housing for pulling the pair of wires. The drive member is drivingly engaged to the transmission structure. The control device further includes an actuator operably coupled to the drive member for effecting movement of the drive member. The transmission structure attains a first length in tension, and attains a second, smaller length in compression.

In accordance with another aspect of the present invention, a control device is provided. The control device includes a housing adapted to be connected to a steerable medical device, such as an endoscope, having at least a pair of control wires, a first drive member for applying tension forces against the pair of control wires, and a plurality of electrical switches that, upon actuation, generate control signals for controlling functions on the medical device.

In accordance with yet another aspect of the present invention, a single use endoscope is provided. The single use endoscope includes an endoscopic device having a proximal end and a distal end. The endoscopic device further has an articulation region proximate the distal end thereof and a pair of control wires extending from the distal end to the proximal end. The single use endoscope also includes a control unit functionally connected to the endoscopic device for deflecting the distal end of the endoscopic device. The control unit includes a drive member, transmission structure, and a plurality of electrical control switches. The single use endoscope further includes a communications conduit connected to the control unit, wherein the communications conduit is adapted to be functionally connected to a control center of an endoscopic imaging system.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

The present invention will now be described with reference to the drawings where like numerals correspond to like elements. Embodiments of the present invention are directed to systems of the type broadly applicable to numerous medical applications in which it is desirable to insert a steerable imaging device, catheter or similar device into a body lumen or passageway. Specifically, embodiments of the present invention are directed to medical systems that include a steerable device and a control device, such as a control handle, that controls the deflection of the distal end of the steerable device as well as controlling other device functions, such as capturing images, discharging fluids, etc. Several embodiments of the present invention include medical devices that incorporate endoscopic features, such as illumination and visualization capabilities, for endoscopically viewing anatomical structures within the body. As such, embodiments of the present invention can be used for a variety of different diagnostic and interventional procedures, including colonoscopy, upper endoscopy, bronchoscopy, thoracoscopy, laparoscopy, ureteroscopy, hysteroscopy and video endoscopy, etc. Although exemplary embodiments of the present invention will be described hereinafter with reference to endoscopes, it will be appreciated that aspects of the present invention have wide application, and may be suitable for use with other medical devices, such as catheters (e.g., guide catheters, electrode catheters, etc.), where manipulation of the distal end by a control handle is desirable. Accordingly, the following descriptions and illustrations herein should be considered illustrative in nature, and thus, not limiting the scope of the present invention, as claimed.

Figure 1:
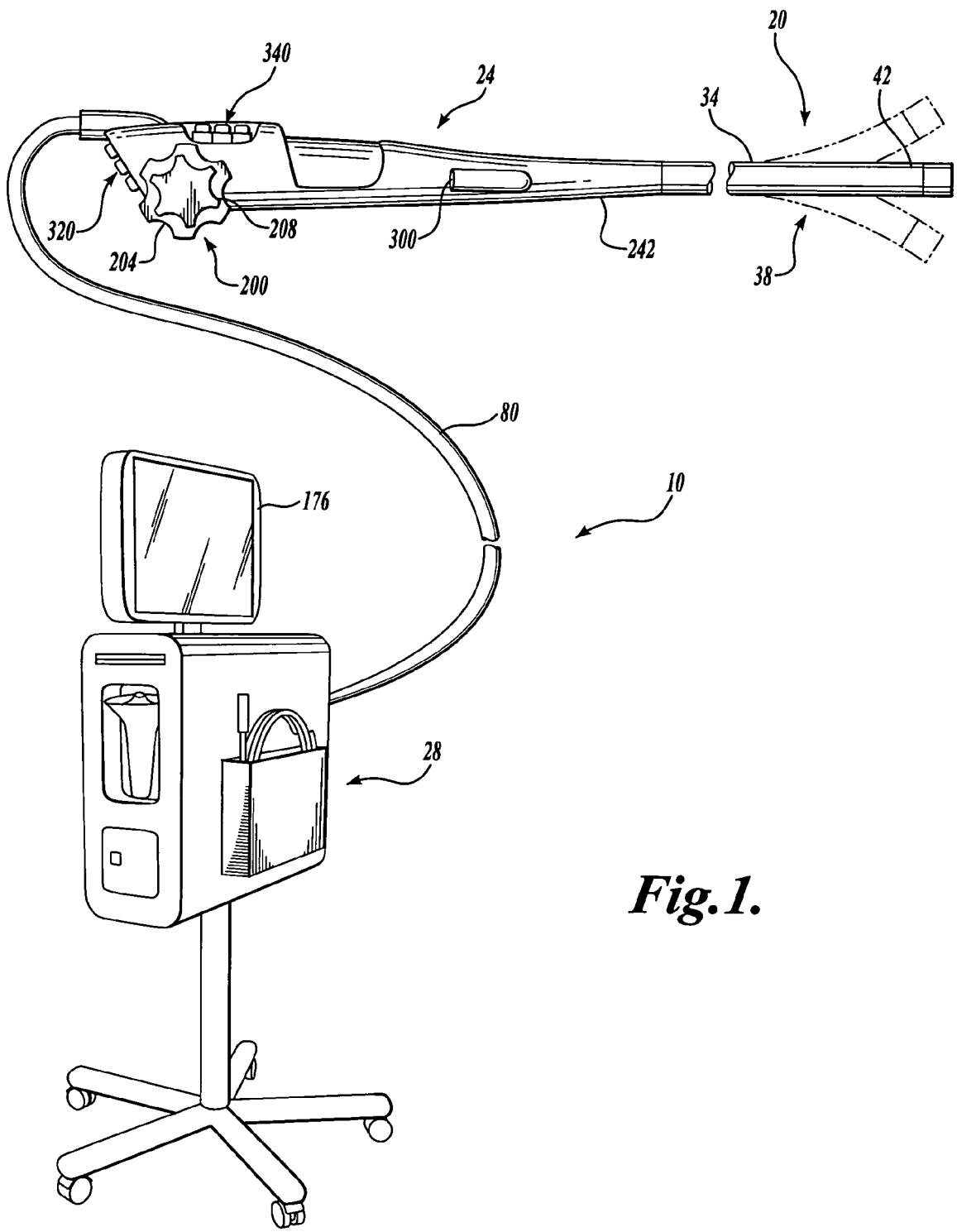
FIG. 1 is a perspective view of one embodiment of an endoscopic imaging system formed in accordance with aspects of the present invention.

FIG. 1 illustrates one exemplary embodiment of an endoscopic video imaging system 10 constructed in accordance with the present invention. The system 10 includes a single use imaging endoscope 20, a control handle 24, and a control cabinet 28. The endoscope 20 is functionally connected and controlled by the control handle 24. The control cabinet 28 is functionally connected to the control handle 24 and functions to provide image processing capabilities, as well as a supply of power, fluids, etc. to the endoscope 20. The single use endoscope 20 can be any flexible, partially-flexible, or rigid elongated steerable probe. The endoscope 20 can be of the optical type (i.e., fiberscope) in which an optical image is carried on a coherent fiber optic bundle, or the video type, in which a miniature camera, which includes a charge coupled device (CCD) or CMOS imaging sensor, is disposed at the distal end of the endoscope 20.

Figure 2:
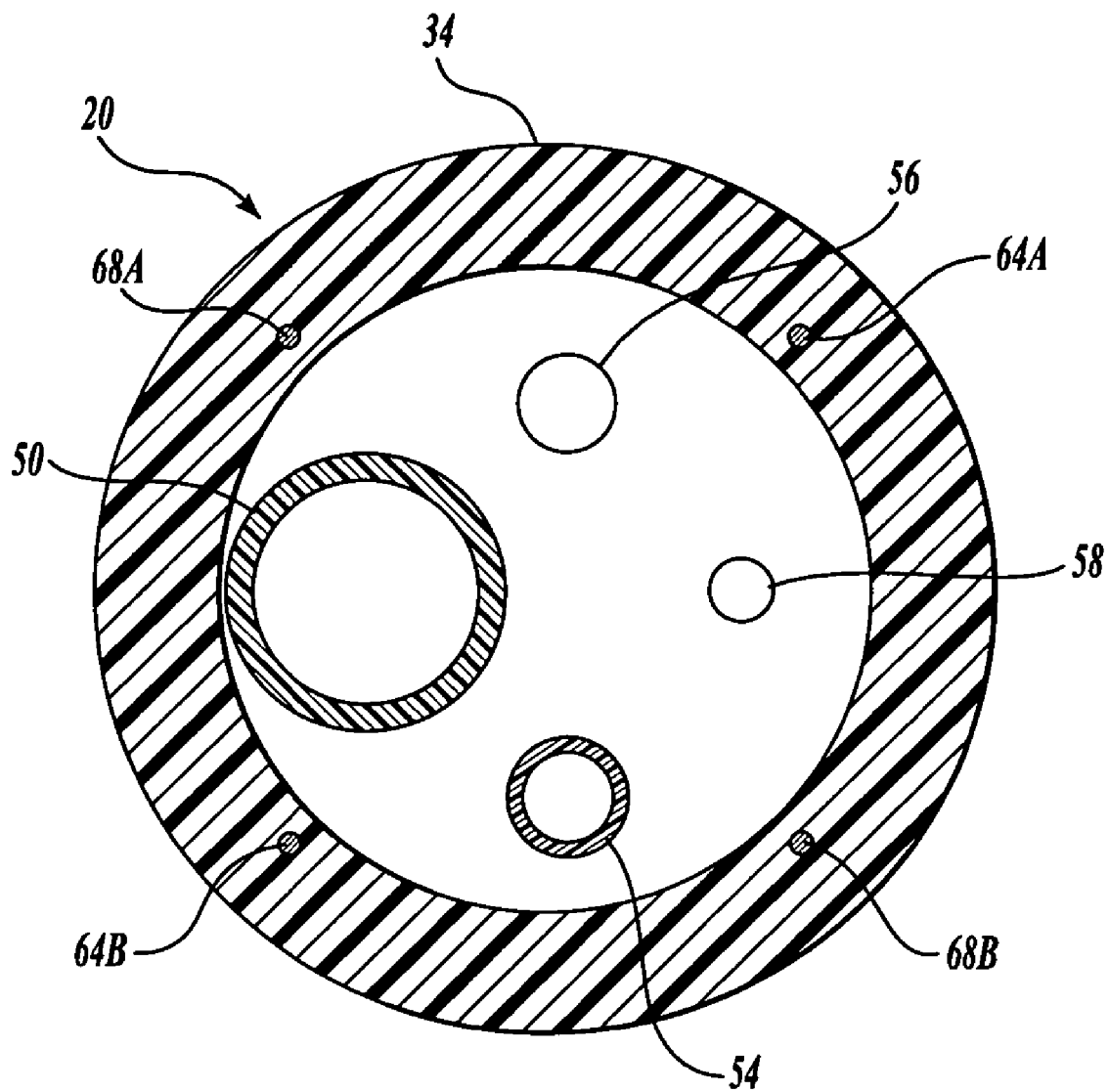
FIG. 2 is a cross sectional view of an endoscope formed in accordance with one embodiment of the present invention.

In one embodiment, the endoscope 20 includes a flexible elongated insertion tube 34 having an articulation section 38 disposed at its distal region, and a distal tip 42. The distal tip 42 of the endoscope 20 includes a digital imaging system (not shown) composed of, in one example, a CMOS image sensor, plastic optics, and LED illumination. The endoscope 20 further includes one or more lumens for the purpose of providing endoscopic procedures, and for the purpose of facilitating the insertion and extraction of fluids, gases, and/or medical devices into and out of the body. For example, the lumens may include a working channel 50, irrigation and/or insufflation lumen 54, and an optional suction lumen (not shown), as best shown in the cross sectional view of FIG. 2. In one embodiment, as will be described in detail below, the working channel 50 also functions as the suction lumen.

The endoscope 20 also includes electrical cables 56 and 58 for supplying power to illumination LEDs and to transmit images back to the control cabinet, respectively. Alternatively, fiber optic cables may be provided for sending and transmitting the same. Each lumen an/or electrical cable extends from the distal tip of the endoscope 20 to the control handle. Finally, the endoscope 20 includes at least one pair of control wires 64A-64B, and preferably two pairs of control wires 64A-64B and 68A-68B, that are connected at the distal tip and terminate through the proximal end of the insertion tube 34.

It will be appreciated that the endoscope 20 may be any single-use or reusable endoscope or similar device, such as a steerable catheter, having a distal tip that is deflectable by at least one pair of control wires. One non-limiting example of a single use endoscope that may be practiced with the present invention is described in co-pending U.S. application Ser. No. 10/811,781, filed Mar. 29, 2004, and U.S. application Ser. No. 10/956,007, entitled "Video Endoscope", filed concurrently herewith the disclosures of which are hereby incorporated by reference.

Returning to FIG. 1, a proximal end of the insertion tube 24 enters the control handle 24, from which a communications conduit 80 emanates. The communications conduit 80 functionally interconnects the control handle 24 to the control cabinet 28. The communication conduit 80 carries image information back to imaging electronics housed in the control cabinet 28 from the imaging sensor. Video related signals are exchanged between the cabinet and the image sensor via electrical cable 58 passing through the insertion tube and the communications conduit 80. As will be described in detail below, video data provided to the control cabinet 28 by the image sensor may be placed in a suitable format for viewing and are transmitted to the video display for viewing by the examining physician. The communications conduit 80 further carries power for illumination LED's forward from the cabinet 28 to the endoscope 20, as well as carrying irrigation/insufflation fluids forward through the insertion tube 34 to the distal tip of the endoscope 20. In one embodiment, vacuum pressure is provided to the working channel through the communications connector 80.

Each of the lumens and electric cables, as well as electrical cables that transmit control signals from the control handle, as will be described in detail below, terminate at the proximal end of the communications conduit in a communications terminal. The terminal is configured to be cooperatively connected to a cabinet terminal for establishing functional connection between the endoscope 20 and the control cabinet 28. As will be described in detail below, appropriate passageways, electrical cables, and the like interconnect the cabinet terminal to the respective components housed in the control cabinet 28.

Figure 3:
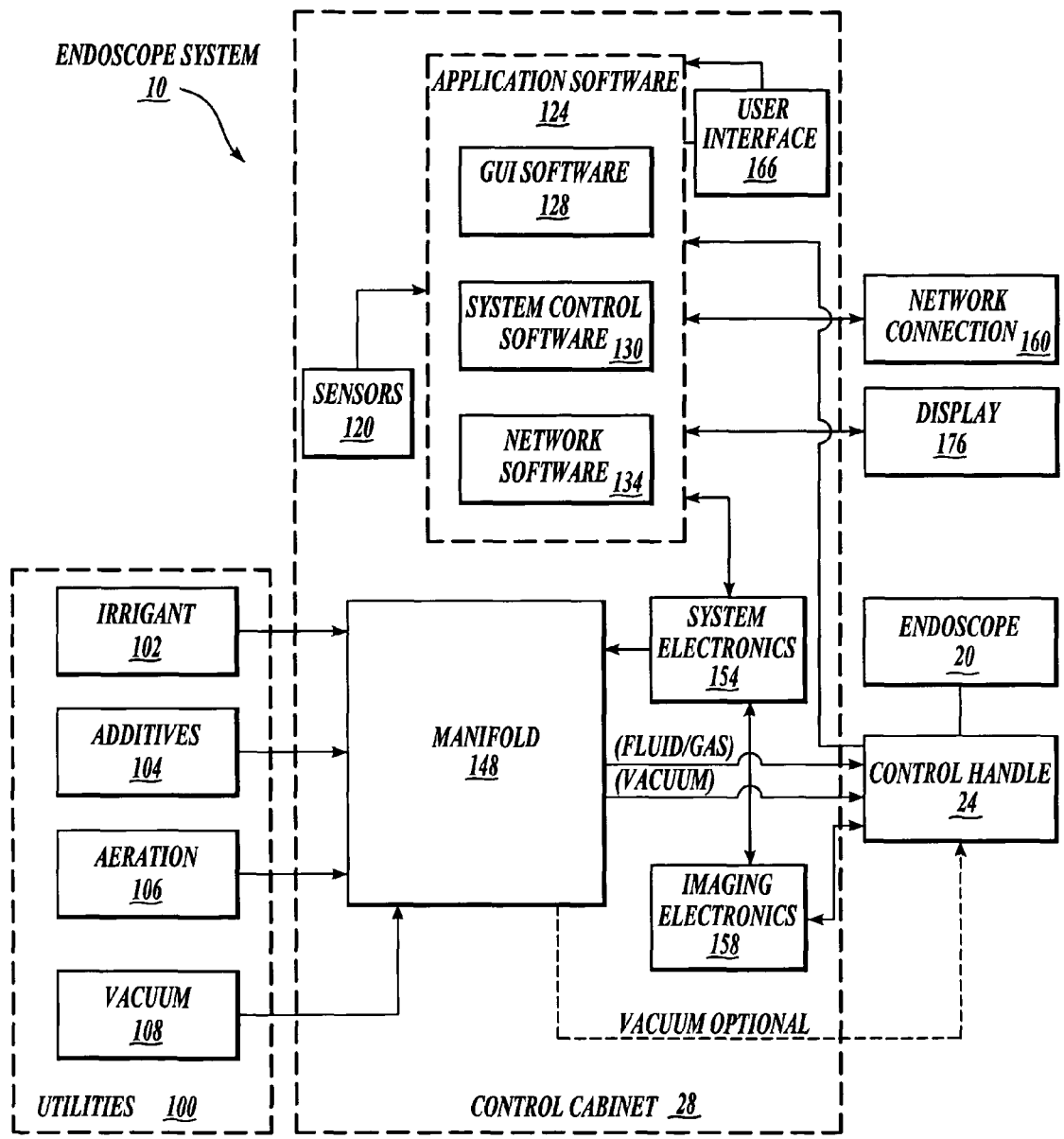
FIG. 3 is a block diagram of one embodiment of the endoscopic imaging system of FIG. 1 formed in accordance with aspects of the present invention.

FIG. 3 is a block diagram of the system 10, including one exemplary embodiment of the control cabinet 28. The control cabinet 28 is preferably mounted on wheels so that it can easily be placed near a patient prior to an examination procedure. The control cabinet 28 is connected to a source of electrical power, either AC mains or a battery, as well as to a plurality of utilities 100, including, for example, an irrigant 102, a solution of additives 104, a supply of aeration 106, and a source of vacuum 108. The control cabinet 28 further includes one or more sensors 120 and a suite of application software 124. Application software 124 further includes a graphical user interface (GUI) software application 128, a system control software application 130, and a network software application 134. In addition, the control cabinet 28 includes a manifold 148, a series of system electronics 154, a an imaging electronics board 158, and a network connection 160. Network connection 160 may include, for example, a local area network or an Internet connection.

Utilities 100 include liquids and/or gases for use in irrigation, such as irrigant 102, additives 104, and aeration 106. Irrigant 102 provides the bulk of the washing medium and consists of, for example, pure water or a saline solution. Additives 104 may include various substances to enhance the wash, such as surfactants, medications, cleaning agents, and other substances added into irrigant 102, either singularly or in combination, upon operator command using control cabinet user interface 166 or controls on the control handle 24. Irrigant 102 and additives 104 are contained in canisters, reservoirs, or other suitable containers that may be external to the control cabinet 28. Aeration 106 is a source of pressurized gas, for example, compressed air, and vacuum 108 is a source of suction. Gases and suction provided in aeration 106 and vacuum 108, respectively, are produced by means of pumps that may be internal or external to the control cabinet 28.

Utilities 100 are in fluid connection with manifold 148, which resides in the control cabinet 28, through a series of piping or other suitable plumbing.

Application software 124, including GUI software application 128, system control software application 130, and network software application 134, resides in the control cabinet 28. GUI software application 128 is well known to those skilled in the art, and provides the physician or operator with live endoscopic video images and, optionally, with visual control and feedback on display 176 using control cabinet user interface 166 or GUI navigational controls on the control handle, as will be described in detail below. System control software application 130 is the central control program of application software 124 that receives input from sensors 120 and user interface/control handle and provides system software control for all features and functions necessary to operate the endoscopic imaging system 10. Sensors 120 may include, for example, pressure transmitters and temperature sensors, and are used for real-time electronic feedback of hardware operating parameters such as pressure and temperature. Network software application 134 enables the operation of network connection 160 and is representative of the hardware and software required for local area network connection and connection to the World Wide Web.

The manifold 148 is a mechanical device that is located in or on the control cabinet 28 and that connects the plumbing of one or more utilities 100, for example, irrigant 102 and additives 104, to one or more appropriate lumens, such as the irrigation/insufflation lumen 54, of endoscope 20 through a series of pipes and other passageways that connect to the control cabinet terminal described above. The manifold 148 includes controllable valves, pumps, and the like, for selectively supplying the utilities 100 to the endoscope 20. The manifold 148 is functionally controlled by the operation of system electronics 154, also contained within the control cabinet 28. Alternatively, insufflation air/gas and irrigation liquid may be connected to the imaging endoscope 20 via a connection (not shown) separate from the communications conduit through a port (not shown) in the control handle 24. The connection connects to the irrigation/insufflation lumen of the endoscope 20. In one embodiment of the invention, the irrigation and insufflation lumen are the same lumen in the imaging endoscope. However, it will be appreciated that separate irrigation and insufflation lumens could be provided if desired and if space in the endoscope permits.

The imaging electronics board 158 receives signals transmitted from an image sensor (not shown) and its associated electronics at the distal end of the endoscope 20. Imaging electronics board 158 is electronically connected to system electronics 154. Application software 124 provides commands to imaging electronics board 158 via system electronics 154. The imaging electronics board 158 can enhance the images received or can provide video effects such as zoom, color changes, highlighting, etc., prior to display of the images on a video display 176. The video display 176 may be formed integrally with the control console or as an external monitor. Images produced by the imaging electronics board 158 may also be printed on a digital printer sent to a network server, saved to a computer readable media such as a floppy disc, CD, DVD, etc., or a video tape for later retrieval and analysis by a physician.

The imaging electronics board 158 also provides electrical power to a light source, such as a number of light emitting diodes (LEDs), at the distal end of the imaging endoscope 20. Alternatively, if the endoscope 20 utilizes an external light source, then the control cabinet 28 can include a light intensity light source, such as a laser or arc lamp source, that supplies light to a fiber optic illumination guide within the imaging endoscope 20 in order to illuminate an internal body organ. As will be described in detail below, the supply of power may be controlled by signals received from the control handle when the user desires to activate the light source or adjust the intensity of light produced. In one embodiment of the invention, the imaging board 158 is provided on a standard PC circuit board to allow individual endoscopes to be tested with a personal computer and without the need for an additional control cabinet 128.

It will be appreciated that the aforementioned description of the control cabinet was done for illustrative purposes only. Accordingly, the control cabinet may have many other configurations and/or features. For example, one embodiment of the control cabinet may include an externally mounted manifold. For a description of non-limiting examples of control cabinets that may be practiced with the present invention, including the use of an external manifold, please see co-pending U.S. application Ser. No. 10/811,781, filed Mar. 29, 2004, and U.S. application Ser. No. 10/956,007, entitled "Video Endoscope", filed concurrently herewith as the disclosures of which are hereby incorporated by reference.

As was described above, the control cabinet 28 is connected to the control handle 24 through the communications conduit 80. As best shown in FIG. 1, the control handle 24 contains a manually actuated steering mechanism 200 for effecting 4-way steering of the articulation section 38 in the up/down direction and in the right/left direction. This mechanism 200 includes an inner knob 204 to control up/down steering and an outer knob 208 to control right/left steering. Alternatively, the inner knob 204 may function to control right/left steering and an outer knob 208 may function to control up/down steering. The knobs 204 and 208 are connected to the articulation section 38 of the insertion tube by means of control wires 64A-64B and 68A-68B (see FIGS. 2 and 5), respectively, that extend through the insertion tube 34. While a manually actuated steering mechanism for effecting 4-way steering of the articulation section is shown, it will be appreciated that a manually actuated steering mechanism that effects 2-way steering may be practiced with and is therefore considered to be within the scope of the present invention.

Figure 5:
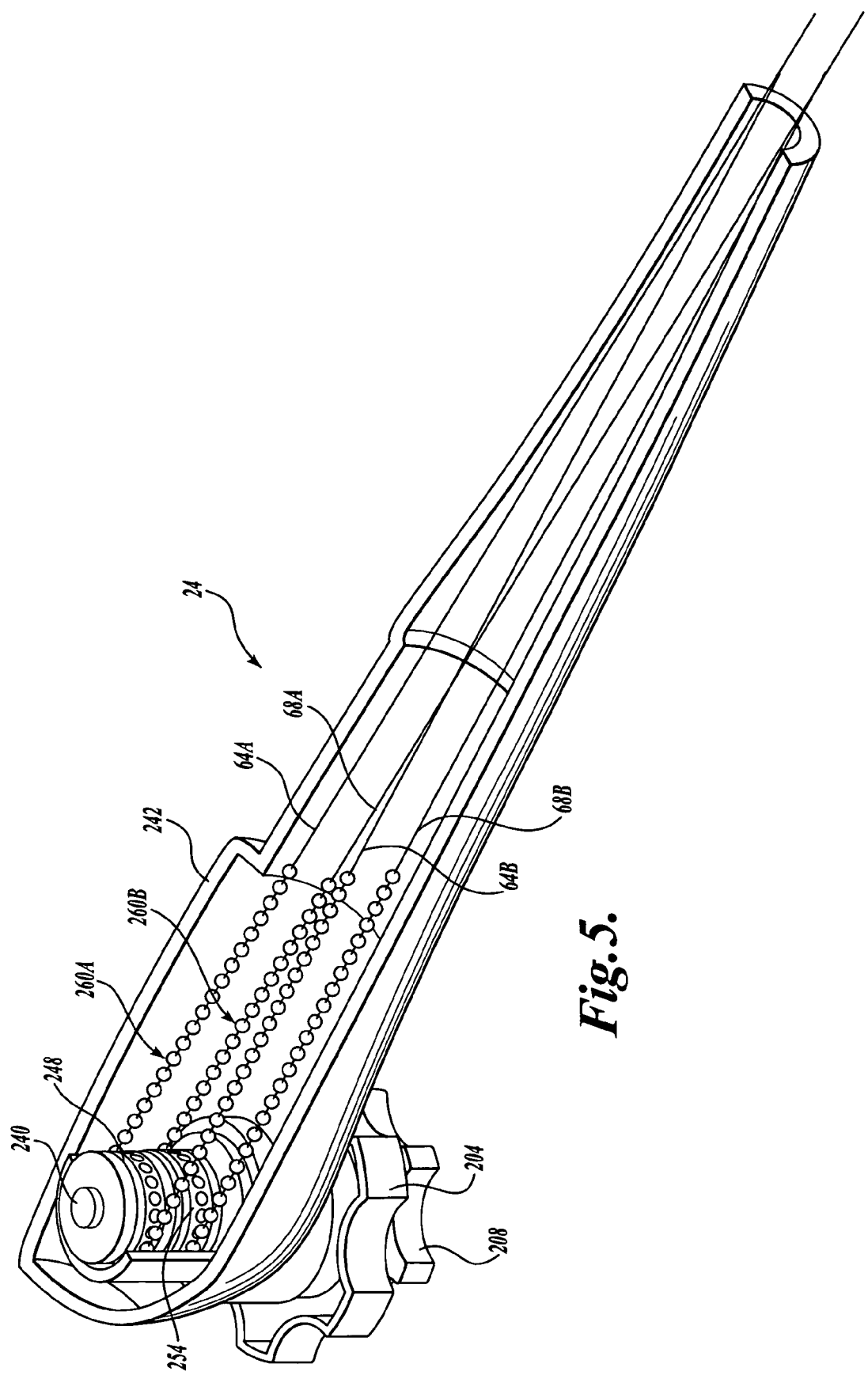
FIG. 5 is a partial cross sectional view of a control handle formed in accordance with one embodiment of the present invention.

In accordance with one aspect of the present invention, the control wires 64A-64B and 68A-68B of the endoscope 20 are operationally connected to the control knobs 204 and 208 in a unique manner. To that end, FIG. 5 illustrates a partial cross sectional view of the control handle 24. A fixed shaft 240 is fixed in the control handle 24 and projects outside the control handle housing 242. An R-L rotary shaft (hidden in FIG. 2) for right and left bending control is rotatably fitted on the fixed shaft 240. An R-L sprocket or gear drive 248 for right and left bending control is engaged with the proximal end portion of the R-L rotary shaft so that the sprocket or gear drive 248 rotates together with the rotary shaft as one unit. Similarly, the control knob 208 is connected to the distal end of the rotary shaft for rotation therewith. A U-D rotary shaft (hidden in FIG. 2) for up and down bending control is rotatably fitted on the outer periphery of the R-L rotary shaft. A U-D sprocket or gear drive 254 for up and down bending control is engaged with the proximal end portion of the U-D rotary shaft so that the sprocket or gear drive 254 rotates together with the rotary shaft as one unit. Similarly, the control knob 204 is connected to the distal end of the rotary shaft for rotation therewith.

Figure 6:
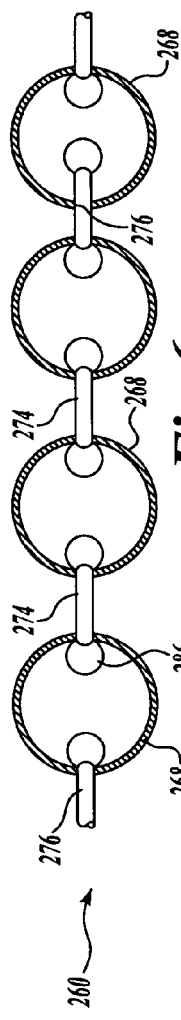
FIG. 6 is a partial side cross sectional view of one embodiment of a bead chain in its extended or tensioned state.
Figure 7:
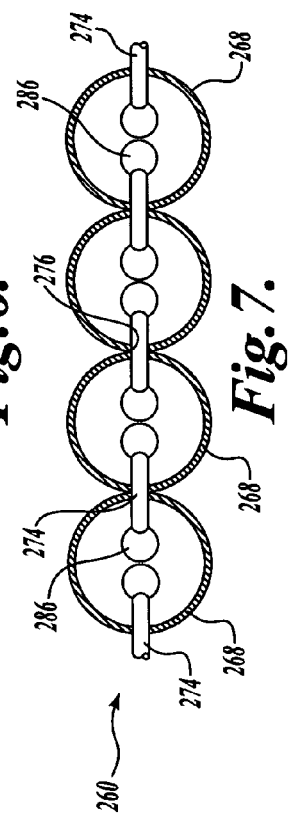
FIG. 7 is a partial side cross sectional view of one embodiment of a bead chain in its collapsed or compressed state.

The proximal end portions of the pairs of control wires 64A-64B and 68A-68B are coupled to first and second lengths of transmission structure or bead chain 260A and 260B, which are wound around the cooperatively configured sprockets or drive gears 248 254, respectively. As best shown in FIGS. 6 and 7, each bead chain 260A and 260B, preferably constructed of stainless steel, comprises a plurality of individual hollow spheres 268, which are interconnected via links 274. The ends of each link 274 are disposed in the inner cavity defined by the spheres through apertures 276. The ends of the links 274 include enlarged heads 286 for slidably retaining the opposite spheres on the link 274.

In use, when tension forces are applied against the spheres 268 as shown in FIG. 6, the bead chain 260 performs in a similar way that a tension wire would and transmits a pull force directly to the control wires 64A-64B and 68A-68B in the system. However, when compression forces are applied against the spheres 268, the slideable connection between the links 274 and the spheres 268 allows the spheres 268 to move together to a collapsed state, as best shown in FIG. 7. In one embodiment, the bead chain 260 collapses on itself approximately one half of its length when not under tension. Such bead chain is well known, and is commonly used for military applications, such as equipment identification, and lamp pull switches. The advantage of using the bead chain 260 is that in compression, it absorbs the slack in the system linearly without having to bow or take up additional space. Additionally, the bead chain 260 enables the control wire system to traverse a drive gear radius that is smaller than is possible with a conventional braided pull wire. In one embodiment, the bead chains 260A and 260B and control wires 64A-64B and 68A-68B are loosely routed through enlarged flexible conduits (not shown) housed in the control handle 24.

Figure 8:
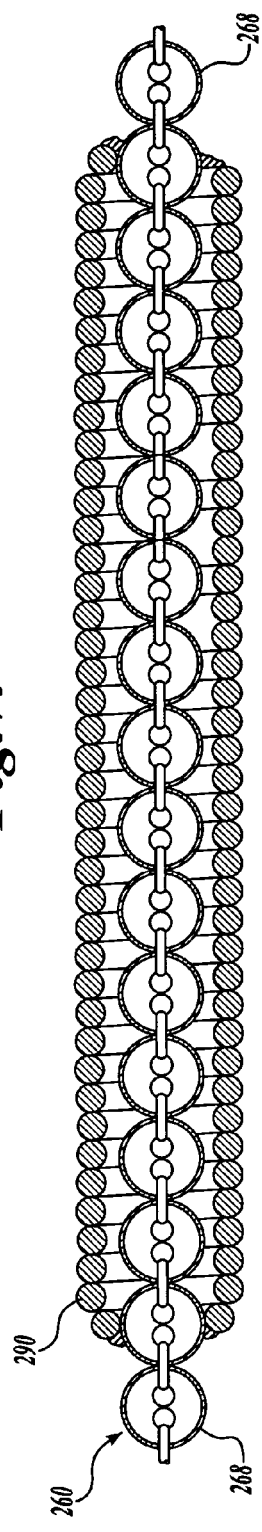
FIG. 8 is a partial side cross sectional view of one embodiment of a bead chain in its collapsed or compressed state, the bead chain being coupled to a biasing member.
Figure 9:
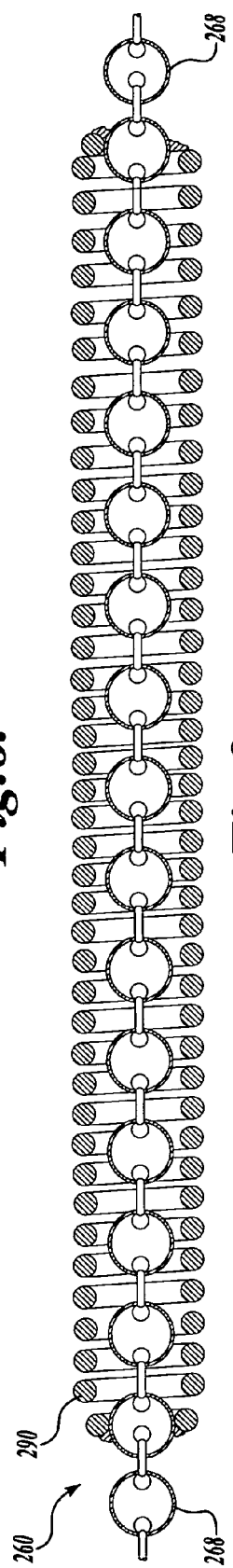
FIG. 9 is a partial side cross sectional view of one embodiment of a bead chain in its extended or tensioned state, the bead chain being coupled to a biasing member.

In another embodiment of the present invention, the spheres 268 of the bead chain 260 may be normally biased into its compressed (e.g. collapsed) state. In one embodiment, a biasing member 290, such as a tension spring, is concentrically arranged over the bead chain 260 and fixedly connected, via welding or the like, at its ends to two spaced apart spheres 268. The biasing member 290 applies a biasing force on the spheres 268. The biasing member helps the bead chain 260 smoothly transition from its compressed or collapsed state, as best shown in FIG. 8, to the tensioned state, as best shown in FIG. 9. The biasing member 290 also helps absorb/relieve slack in the system as the insertion tube of the device is looped. In other embodiments, the biasing member may be a rubber or elastomeric sheath, although any elastically recoverable member may be used.

In some embodiments, the transmission structure, such as the bead chains, are connected directly to the control wires. In other embodiments of the present invention, the transmission structure, such as the bead chains, are connected to the control wires using a spring or other biasing member (not shown). In such embodiments, the biasing members 290 discussed above may be omitted. It will be appreciated that the stiffness of the biasing member that interconnects the control wires and the transmission structure can be adjusted to maintain uniform tension in the system during use. Alternatively, the biasing members, such as springs, may be positioned at the distal end of the device for interconnecting the distal ends of the control wires to the distal end of the device.

While the mechanism 200 was shown and described herein, it will be appreciated that other well known or future developed mechanisms for effecting either 2-way or 4-way steering may be practiced with the present invention. For several examples, please see U.S. Pat. Nos. 5,007,406, 4,742,816, 4,762,119, 4,078,555, 4,461,282, and 4,207,873, the disclosures of which are hereby incorporated by reference. Additionally, control knobs were shown for rotating the sprockets or drive gears, however, other actuators, such as levers, may be used.

The control handle 25 may further include an entrance port 300 formed in the exterior surface of the control handle housing 242. The entrance port 300 provides access to the working channel 50 described above. In one embodiment, the entrance port 300 may include an attachment point for a vacuum line (see FIG. 3) that collects liquids or debris received from a lumen within the endoscope and deposits it in a collector, such as a collection bottle, at the utilities 100. The vacuum collection bottle may be controlled by a vacuum valve (not shown) that is positioned in the control handle. Alternatively, in the preferred embodiment, the valve can be positioned within the control cabinet 28 in manifold 148 and controlled via control signals generated by the control handle 24. The control handle 24 may include other control switches that generated control signals, as will be described in detail below.

Figure 4:
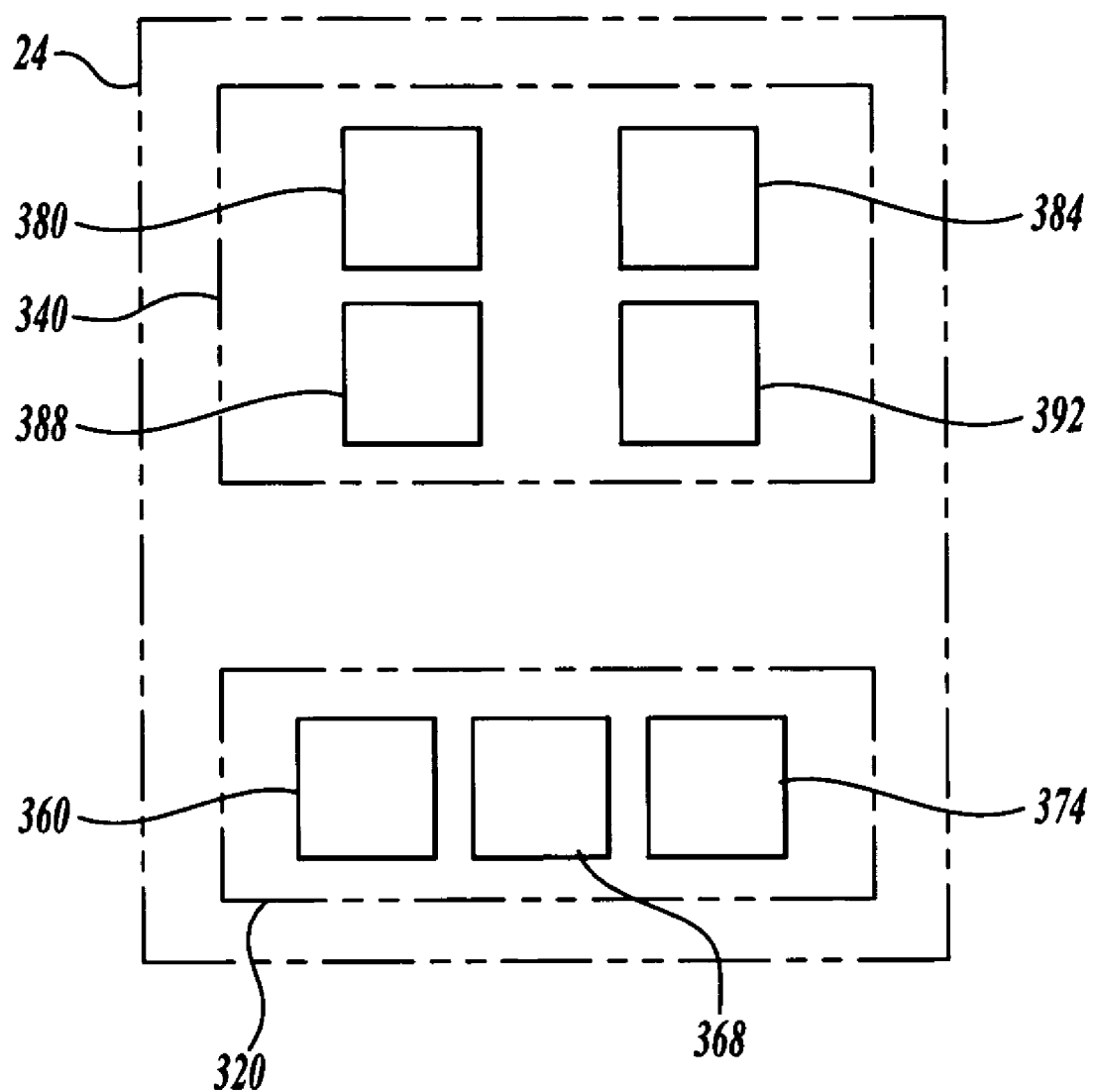
FIG. 4 is a block diagram of one embodiment of a control handle formed in accordance with aspects of the present invention

FIG. 4 illustrates one exemplary embodiment of a block diagram depicting two sets 320 and 340 of control switches for operating various control functions of the system 10. While a few functions will be described below, it will be appreciated that the control signals generated from the control switches may be used for any function or operation of the endoscopic imaging system 10. The sets 320 and 340 of control switches are positioned in an ergonomic arrangement on the control handle 24, and may be actuated with manual depression by the operator. The control switches are connected in electrical communication with the appropriate system component of control cabinet 28, such as the application software 124, through electrical cabling, which is routed through the communications conduit 80. Alternatively, the control signals may be transmitted via a wireless radio frequency channel, an infrared or other optical link.

The first set 320 of switches are located at the back end of the control handle and includes an image control switch 360, a menu switch 368, and a GUI navigational switch 374. The image control switch 360 may be used to capture an image of an internal body cavity or organ in which the endoscope is placed or adjust the image being received from the endoscope. In one embodiment, the images collected may be still images or video images. The images may be adjusted for contrast or otherwise enhanced prior to display or stored on a recordable media. The menu switch 368 allows the operator to display the menu of the video display 176, and the GUI navigational switch 374 allows the operator to navigate the menu displayed on the video display 176 to input various data for controlling the endoscope 20. The navigational switch 374 is preferably a 5-way switch having up, down, right, left, and enter command capabilities.

The second set 340 of switches are located along the side of the control handle housing 242 and includes a suction switch 380, an irrigation switch 384, an insufflation switch 388, and bolus wash switch 392. The irrigation switch 384 activates an irrigation source to supply a liquid such as water through an irrigation lumen of the endoscope 20. The liquid serves to clean a window in front of an image sensor and/or the light source at the distal end of the endoscope 20 as well as an area of the body cavity. The insufflation switch 388 is provided to activate the insufflation source to supply air/gas through a lumen of the endoscope 20. The supply of the insufflation gas expands portions of the body cavity around the distal tip of the endoscope 20 so that the physician can more easily advance the endoscope or better see the tissue in front of the endoscope 20. The suction switch 380 activates a vacuum source to supply vacuum pressure through a lumen of the endoscope 20. The supply of vacuum removes fluid and debris from inside the patient's passageway.

In one embodiment, the one or more of the control switches used may be configured to generate two separate signals based on the distance of actuator travel. As such, depending on the amount of switch depression, one of two control signals is generated and transmitted to the cabinet 28. One such switch is commonly referred to as a "Double-Action Light Touch Switch," and is commercially available from Panasonic.

In one embodiment of the present invention, the endoscopic device 20, control handle 24, and communications conduit 80 (hereinafter "the single-use endoscope") may be used for single use application. Thus, upon completion of a patient examination procedure, the single use endoscope is disconnected from the control cabinet 28 and disposed of. A new single-use endoscope is then connected to the control cabinet 28 for the next examination procedure to be performed.

While the preferred embodiment of the invention has been illustrated and described, it will be appreciated that various changes can be made therein without departing from the spirit and scope of the invention. It is therefore intended that the scope of the invention be determined from the following claims and equivalents thereof.

The embodiments of the invention in which an exclusive property or privilege is claimed are defined as follows:

1. A control device for use with a steerable medical device, comprising:
    at least one pair of control wires for deflecting the distal end of the medical device, wherein each control wire has a proximal end;
    a housing configured for receiving the pair of control wires;
    an elongate transmission structure having a longitudinal axis, a first end, and a second end, wherein each end is coupled to one of the proximal ends of the pair of control wires;
    the transmission structure having a number of bodies that slidably engage links, wherein a pair of adjacent bodies slidably move toward each other along the longitudinal axis of the transmission structure to receive a compressive force applied to the transmission structure, and the pair of adjacent bodies slidably move away from each other generally along the longitudinal axis of the transmission structure to receive a tensile force applied to the transmission structure;
    a drive member for engaging the transmission structure; and
    an actuator operably coupled to the drive member for effecting movement of the drive member.

2. The control device of claim 1, wherein the transmission structure is a bead chain.

3. The control device of claim 1, wherein the tensile force applied to the transmission structure is transmitted through a link disposed between the pair of adjacent bodies.

4. The control device of claim 3, wherein the link includes two ends that slidingly engage the pair of adjacent bodies.

5. The control device of claim 4, wherein the pair of adjacent bodies are both generally hollow.

6. The control device of claim 5, wherein the pair of adjacent bodies each has an aperture configured to receive one of the ends of the link.

7. The control device of claim 1, wherein the drive member contains a recess configured to receive part of the number of bodies.

8. The control device of claim 1, wherein the first end of the transmission structure includes adjacent bodies that are located next to each other and the second end of the transmission structure includes adjacent bodies that are located apart from each other.

9. The control device of claim 8, wherein the first end of the transmission structure is coupled to a first control wire under compression and the second end of the transmission structure is coupled to a second control wire under tension.

10. A control handle for a steerable medical device, comprising:
    a handle housing adapted to be connected to a shaft of a steerable medical device having at least a pair of control wires therein that are tensioned to orient the medical device in a desired direction;
    a drive member within the handle housing for applying tension forces against the pair of control wires; and
    a bead chain that connects the drive member to at least one control wire of the pair of control wires, the bead chain having a number of bodies that are slidably movable along a longitudinal axis of the bead chain in relation to each other, wherein a first part of the bead chain includes two adjacent bodies that are separated from each other and a second part of the bead chain that is different to the first part and includes two adjacent bodies that are located next to each other.

11. The control device of claim 10, wherein the bead chain at least partially wraps around the drive member such that the first part of the bead chain is located on one side of the drive member and the second part of the bead chain is located on the other side of the drive member.

12. The control device of claim 10, further including a plurality of electrical switches on the handle housing that, upon actuation, generate control signals for controlling functions of the steerable medical device.

13. A steerable medical device, comprising:
    a shaft having a proximal end and a distal end;
    two control wires having two distal ends secured at or adjacent the distal end of the shaft and two proximal ends that are selectively tensioned to orient the distal end of the shaft in two desired directions;
    a handle at the proximal end of the shaft that includes two actuators for selectively tensioning the two control wires; and
    two chains in-line with the two control wires, each chain having a number of bodies that are joined by links that slidably move relative to the bodies along a longitudinal axis of the chain so that some of the bodies are separate from each other while, simultaneously, some other bodies engage with each other.

14. The steerable medical device of claim 13, wherein at least one of the two chains is a bead chain.

15. The control device of claim 13, wherein the two actuators are mounted about a common shaft.

* * * * *